US008623496B2

(12) United States Patent
Blick et al.

(10) Patent No.: US 8,623,496 B2
(45) Date of Patent: Jan. 7, 2014

(54) LASER DRILLING TECHNIQUE FOR CREATING NANOSCALE HOLES

(75) Inventors: Robert H. Blick, Madison, WI (US); Minrui Yu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 693 days.

(21) Appl. No.: 12/614,237

(22) Filed: Nov. 6, 2009

(65) Prior Publication Data

US 2011/0111179 A1 May 12, 2011

(51) Int. Cl.
*B32B 3/10* (2006.01)

(52) U.S. Cl.
USPC ........... 428/172; 428/131; 428/132; 264/400; 204/403.01; 438/1

(58) Field of Classification Search
USPC ..................................... 428/172; 219/121.85
See application file for complete search history.

(56) References Cited

U.S. PATENT DOCUMENTS

| 6,758,961 B1 * | 7/2004 | Vogel et al. ................. 205/777.5 |
| 2005/0009171 A1 | 1/2005 | Fertig et al. |
| 2006/0049156 A1 | 3/2006 | Mulloy et al. |

OTHER PUBLICATIONS

Fertig, N., George, M., Klau, M., Meyer, C., Tilke, A., Sobotta, C., Blick, R., Behrends, J.; "Microstructured Apertures in Planar Glass Substrates for Ion Channel Research": Taylor and Francis (2003).*

Kaplan, Steven M. (2004). Wiley Electrical and Electronics Engineering Dictionary. Wiley—IEEE Press. Online version available at: http://www.knovel.com/web/portal/browse/display?_EXT_KNOVEL_DISPLAY_bookid=3663&VerticalID=0.*

Kopitkovas, G.; Lippert, T.; David, C.; Wokaun, A.; Gobrecht, J., "Fabrication of microoptical elements in quartz by laser indued backside wet etching": Microelectronic Engineering (2003), 67-68, 438-444.*

Yu, M., Kim, H, Blick, R.; "Laser Drilling of Nano-pores in Sandwiched Thin Glass Membranes": Optcs Express (03132009). vol. 17, No. 12.*

Fertig, N., et al, Whole Cell Patch Clamp Recording Performed on a Planar Glass Chip, Jun. 2002, Biophysical Journal, vol. 82, pp. 3056-3062.*

Fertig, Niels, et al., Microstructured Apertures in Planar Glass Substrates for Ion Channel Research, Receptors and Channels, 9, pp. 29-40, 2003, Taylor & Francis, Oxford, UK.

Fertig, N., et al., Microstructured Glass Chip for Ion-Channel Electrophysiology, Physical Review E., Vo. 64, 040901(R), pp. 1-4, American Physical Society, College Park, MD, USA, 2001.

Fertig, Niels et al., Whole Cell Patch Clamp Recording Performed on a Planar Glass Chip, Biophysical Journal, Vo. 82, Jun. 2002, pp. 3056-3062, Biophysical Society, Bethesda, MD, USA.

(Continued)

*Primary Examiner* — Maria Veronica Ewald
*Assistant Examiner* — Brian Handville
(74) *Attorney, Agent, or Firm* — Boyle Fredrickson S.C.

(57) ABSTRACT

A method of forming extremely small pores in a substrate that is used, for example, in patch clamp applications is provided that employs an energy absorbing material beyond a back side of the substrate to allow a laser to be focused adjacent the exit side of the substrate so as to generate a pore through the substrate and can also form a crater in the back side of the substrate and in which the pore may propagate from the crater in a drilling direction that can oppose a laser transmission direction.

7 Claims, 8 Drawing Sheets

(56) References Cited

OTHER PUBLICATIONS

Fertig, Niels, et al., Activity of Single Ion Channel Proteins Detected with a Planar Microstructure, Applied Physics Letters, vol. 81, No. 25, pp. 4865-4867, Dec. 16, 2002, American Institute of Physics, College Park, MD, USA.

Fertig, N., et al., Stable Integration of Isolated Cell Membrane Patches in a Nanomachined Aperture, Applied Physics Letters, vol. 77, No. 8, pp. 1218-1220, Aug. 21, 2000, American Institute of Physics, College Park, MD, USA.

U.S. Appl. No. 12/277,900, filed Nov. 25, 2008; First Named Inventor Robert H. Blick; Entitled: Retro-Percussive Technique for Creating Nanoscale Holes.

Yu, Minrui et al., Laser Drilling of Nano-pores in Sandwiched Thin Glass Membranes, Optical Society of America, Jun. 8, 2009, vol. 17, No. 12, pp. 10044-10049.

Lehnert, T., et al., Glass Reflow on 3-Dimensional Micro-Apertures for Electrophysical Measurements On-Chip Aug. 18, 2006.

* cited by examiner

LASER DRILLING TECHNIQUE FOR CREATING NANOSCALE HOLES

STATEMENT REGARDING FEDERALLY SPONSORED RESEARCH OR DEVELOPMENT

This invention was made with United States government support awarded by the following agency: NSF 0520527. The United States government has certain rights in this invention.

CROSS REFERENCE TO RELATED APPLICATION

N/A.

BACKGROUND OF THE INVENTION

The present invention relates to electrophysiology and "patch clamping" for investigating ionic and molecular transport through cellular membranes via ion channels and, in particular, to a substrate providing a set of nano to microscale pores that may be readily sealed to cellular membranes. Ion channel investigation using patch clamps often plays an important role in drug discovery and preliminary drug screening or evaluation, for example, by providing a model that shows an effect of a drug on ion channels. Doing so can be useful for either avoiding adverse effects or for creating a positive therapeutic effect for the treatment of ion channel related diseases.

Drug screening can require a large number of ion channel measurements. Accordingly, in current practice, planar patch clamps are preferable because they allow parallelization of multiple samples on a substrate, often referred to as a wafer, chip, or well-plate, and facilitate measurement automation. Each sample has a cell or cell wall that is positioned so that an ion channel in the cell or cell wall is aligned with a pore at the sample site. The cell or cell wall is sealed to the patch clamp substrate in a manner that allows a small amount of electrical current to be used in performing ion channel investigations, typically by way of an extremely high resistance seal between the patch clamp substrate and the cell wall (a gigaohm seal or gigaseal). Gigaohm seals achieved using on-chip patch clamp procedures usually have electrical resistance values of about 1 gigaohm, with resistance values of up to about 5 gigaohms being achieved in some relatively rare instances.

Planar patch clamp substrates can be made from, for example, silicon, Teflon®, PDMS (polydimethylsiloxane), PSG (phosphosilicate glass), or glass. While such materials prove suitable for many planar patch clamp implementations, a single crystal quartz (quartz) material can be a particularly desirable for making planar patch clamp substrates. Quartz exhibits particularly high electrical insulating properties and is piezoelectric. Its unique electrical characteristics allow it to be used as a patch clamp substrate by providing very low levels of background noise while performing ion channel investigations. Furthermore, quartz exhibits particularly good mechanical characteristics such as, for example, good hardness, thermal stability, and chemical stability characteristics. Despite a general recognition of quartz's suitability for use as a patch clamp substrate, many of its desirable characteristics, such as hardness, make fabricating (micromachining) the pores in a quartz substrate rather difficult and/or time consuming.

Traditionally, micromachining of quartz is performed using a combination of lithography and reactive ion etching (RIE). However, RIE techniques require multiple steps and are relatively slow processes.

Another method of micromachining quartz is by way of direct laser beam ablation. During direct laser beam ablation, a high power density, short pulse width femtosecond laser beam is irradiated directly onto quartz. The nonlinear interaction between the ultrafast laser pulses and quartz, which has a band gap of about 9 eV, results in a cyclic multiphoton absorption and electron excitation between the ground and excited states. During this process, the initial excited electrons induce an avalanche ionization and generate a microplasma which ablates the quartz. However, since quartz has a wide band gap, this approach is also slow and is limited in terms of pore diameter and material thickness that can be achieved.

Recently, numerous advances have been made in micromachining of pores in non-quartz substrates, for example, by utilizing nanosecond lasers, such as excimer lasers instead of femtosecond lasers. Excimer lasers, which emit ultraviolet (UV) light, have been successfully implemented in relatively fast drilling procedures in non-quartz materials. However, quartz has excellent optical transmission over a large spectrum, from UV to infrared (IR), whereby it is transparent to light(s) in this spectrum. Since quartz is transparent to and therefore substantially unaffected by UV light(s), it has been widely accepted that excimer lasers are not usable for micromachining quartz.

Furthermore, although various patch clamping and other techniques have been developed and, at least to some extent, standardized for successfully modeling and investigating ion channel function voltage-sensitive (or voltage-gated) ion channels, in-depth investigation of yet other types of ion channels, such as mechanosensitive ion channels, remains at least somewhat frustrating and/or impracticable. Accordingly, numerous molecular mechanisms and their functionalities within mechanosensitive ion channels remain unknown, whereby cellular responses to mechanical stimuli remain some of the least understood of the known sensory mechanisms.

SUMMARY OF THE INVENTION

The present invention provides an improved technique for the generation of nanoscale-sized pores, for example, pores having diameters of nearly 200 nm, using a laser through a substrate that is substantially transparent to the laser's emitted wavelength and therefore tends to be unaffected by the laser using previously known practices. In the technique, the substrate is backed by an energy absorbing material that has relatively high coefficients of thermal expansion and UV absorption. The laser light is transmitted through the substrate and focused adjacent a back side of the substrate, for example, at or immediately in front of or behind an interface defined between the substrate and energy-absorbing material. Doing so can increase a temperature of the energy-absorbing material which, in turn, heat the substrate from beyond its back side. Heating the energy-absorbing material in this manner increases the temperature of the substrate to an extent that melts the substrate, and correspondingly facilitates melting-type formation of small diameter smooth pores and can also lead to formation of a crater(s) at the back side of the substrate. According to some aspects of the invention, the crater can be formed by a shock wave that results from thermal expansion of the energy absorbing material, but in any event, is formed by ablation or other thermal related removal of material from the back side of the substrate. The pore and/or crater are therefore created by a sandwich drilling or sandwich drilling-like technique that can give the pore and/or crater, of the quartz chip, surface characteristics that are similar to surface characteristics of pipettes that have been fire-polished with open flame procedures. In other words, the pore(s) and/or crater(s) formed according to aspects of the present invention have surfaces that are substantially smooth, their surface irregularities having been removed or attenuated by surface tension induced flowing of melted material in such irregularities which tends to smooth the same.

Specifically then, the present invention provides a method of creating nanoscale holes by using steps including creating a multi-layered assembly that comprises a substrate material and an energy absorbing material. The substrate material receives the nanoscale hole and defines a front side and an opposing back side. The energy absorbing material is adjacent the back side of the substrate material. A laser is applied through the multi-layered assembly, by initially passing through the substrate material and being focused at and absorbed by the energy absorbing material, increasing a temperature of the back side of the substrate material to a greater extent than an increase in temperature of the front side of the substrate material. Continued application of such laser stimulus to the energy absorbing material may correspondingly heat and/or pressurize the back side of the substrate, which can initiate a drilling of or establishing a pore through the substrate.

It is therefore an object of at least one embodiment of the invention to utilize a laser to drill a pore in a substrate by indirectly heating the substrate by focusing the laser at or near an interface between the substrate and an energy absorbing material. This allows for laser micromachining of a material that might otherwise be transparent to light of a wavelength emitted by the laser.

The method can further include a step of producing a crater at the back side of the substrate material which, in some embodiments, can be produced by a shock wave that increases both a temperature and a pressure at an interface defined between the back side of the substrate material and the energy absorbing material. The crater formation can be an initiating step for drilling of the pore and the pore, in some embodiments, is drilled in a drilling direction that opposes a direction of laser transmission through the substrate.

It is thus an object of at least one embodiment of the invention to provide a method for forming craters in back sides of substrates and/or drilling pores from the crater toward the front side of the substrate.

The substrate material may be a single crystal quartz material and the laser can be a UV emitting excimer laser or other lasers, e.g., CO2 lasers, and/or others.

It is therefore an object of at least one embodiment of the invention to generate pores and/or craters in a single crystal quartz wafer or chip and may be a further object of at least one embodiment of the invention to perform laser micromachining on a substrate that is substantially transparent to a wavelength of light that is emitted by the laser.

The energy absorbing material may be a liquid media, for example, an ultraviolet radiation absorbing organic liquid such as acetone and/or fluorescence immersion oil. Such liquid media can have a thermal expansion coefficient of at least about $700 \times 10^{-6}$ $K^{-1}$ and an ultraviolet absorption coefficient of at least about 1.46 $cm^{-1}$, for example, an ultraviolet absorption coefficient of between about 1.46 $cm^{-1}$ to 1.65 $cm^{-1}$.

It is thus an object of at least one embodiment of the invention to provide a liquid medium for use as an energy absorbing material that can be placed under the substrate for performing a laser induce backside etching of the back side of the substrate. The backside etching may be performed on a quartz chip that has been pre-etched or thinned from an initially thick substrate. The initially thick substrate may be about 100-500 microns thick and can be either laser or wet etched, for example, with a buffered oxide etchant (BOE) or hydrofluoric (HF) etchant, in a pre-thinning procedure, down to about 20-50 microns in thickness before the nanopore laser drilling is initiated, which may improve suction and reduce series resistance.

The pore can have a smaller diameter than the crater which it intersects, and the pore diameter can be generally constant along its length or a major portion thereof, and a crater sidewall can include an undercut or groove extending thereinto.

It is thus an object of at least one embodiment of the invention to provide a patch clamp chip that has a smooth pore that opens into a relatively larger diameter crater. This configuration can provide suitable structure to which a cell can be mounted.

DETAILED DESCRIPTION OF THE PREFERRED EMBODIMENT

Figure 1:
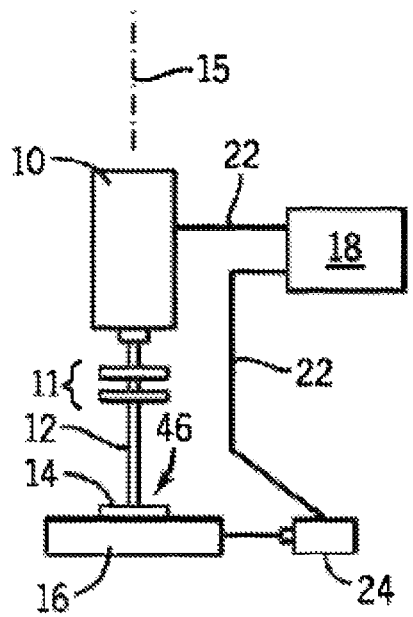
FIG. 1 is a schematic diagram of an apparatus used for producing a planar patch clamp chip or wafer per from a multi-layered assembly one embodiment of the present invention.

Referring now to FIG. 1, the present invention may use an ArF excimer laser 10 having collimating and focusing optics 11 to direct a narrow collimated beam 12 of light along an axis 15 toward a back surface of a sandwich-like, multi-layered assembly 14 that is held on a mechanical stage 16. The laser may, for example, have a wavelength range of about 155 nm to about 195 nm and is preferably operated to emit a beam 12 of light having a wavelength of about 193 nm. In other embodiments, laser 10 may be yet other types of lasers, such as CO2 lasers, and/or others, depending on, for example, a desired wavelength that is selected based on particular characteristics of components within the multi-layered assembly 14, in other words, how the multi-layered assembly 14 reacts to exposure to light having such wavelength(s), and/or other factors.

The laser 10 may include a variable attenuating mirror for controlling how much of the laser beam is to be transmitted, and a stencil metal mask with an adjustable aperture that allows production of different laser beam shapes and sizes. Laser 10 may further include a stage 16 that can be controlled by an automated controller 18 of the type well known in the art for providing control signals 22 to the laser 10, controlling its output power in a series of pulses as will be described and providing control signals 22 to actuator motors 24 providing x-y control of the stage 16.

Figure 2:
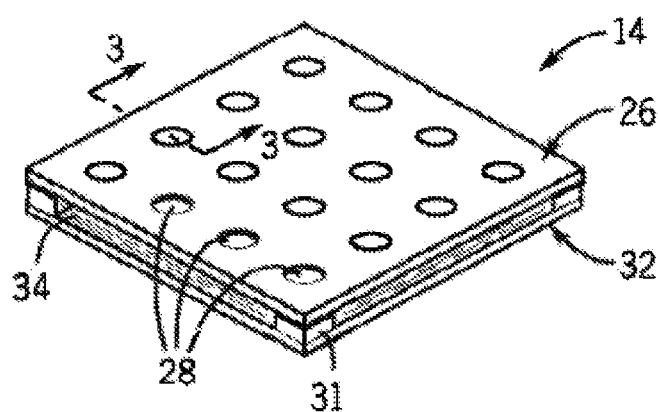
FIG. 2 is a pictorial view of the multi-layered assembly used in the machine of FIG. 1.
Figure 3:
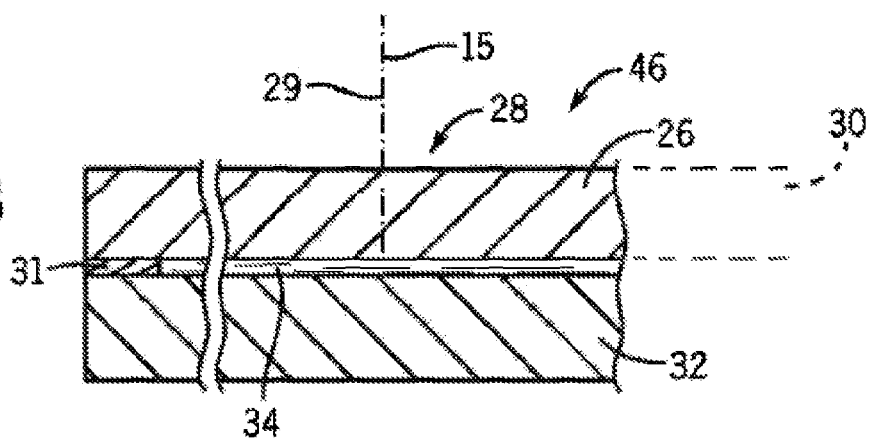
FIG. 3 is a cross-section along line 3-3 of FIG. 2 showing a spacing of a substrate from a backer plate by a gap filled with an energy absorbing material.

Referring now to FIGS. 2 and 3, the multi-layered assembly 14 may include a substrate 26, an underlying energy absorbing material 34, and a backer plate 32 that supports the energy absorbing material 34 and substrate 26. The energy absorbing material 34 cooperates with the substrate 26 to perform a one-step micromachining process in which the laser 10 drills through the substrate 26, forming small diameter smooth holes therethrough, while causing a nominal amount of surface roughness to the substrate 26. For example, a synergistic relationship between the energy absorbing material 34 and the substrate 26 allow for using the laser 10 to perform a one-step micromachining process to create holes or pores that have diameters as small as 200 nm, while resulting in an end-of-procedure surface roughness of merely tens of nanometers as measured from the respective surface(s) of the substrate 26. Furthermore, submicrometer holes, bores, or pores may be formed in the substrate 26 along with crater-shaped depressions that are formed in a surface of the substrate that faces a direction of back from the substrate. Such relationships between the components of multi-layered assembly 14, and techniques for forming such hole, pores, and craters in the one-step micromachining procedure, are discussed in greater detail elsewhere herein.

Still referring to FIGS. 2 and 3, within the multi-layered assembly 14, substrate 26 can be, for example, a clear solid material that is transparent to the UV light emitted by laser 10 (FIG. 1), preferably a single crystal quartz chip or wafer. A suitable such single crystal quartz wafer for use as substrate 26 is the 350 μm thick quartz wafer that is readily available from the University Wafer Company of South Boston, Mass.

A front surface of the upper substrate 26 may have a series of depressions or wells 28 formed at regular x-y grid locations 29. The wells 28 provide a thinned portion 30 at the locations 29 measured along axis 15 having a thickness of 100 to 1000 g and may be molded, ground, or etched in the substrate 26. The diameter of the wells 28 may be relatively large, for example, 5.0 mm, and serve simply to permit a generally thicker substrate 26 in regions outside of the locations 29 for structural convenience. Referring specifically to FIG. 2, the substrate 26 can define a single, unitary structure with multiple wells 28 formed therein. However, it is also contemplated that substrate 26 can be an assembly of multiple, relatively smaller, individual quartz wafers or chips, each having only a single well 28 formed therein.

Referring yet further to FIGS. 2 and 3, in some embodiments, backer plate 32 is positioned as a lowermost component of the multi-layered assembly 14 and can serve as, for example, a structural base or part of a structural frame thereto. Backer plate 32 may be a supportive slide that is incorporated into the multi-layered assembly 14, underlying and being spaced vertically below the substrate 26. Optional spacer 31 is one suitable structure that can be used to establish such vertical spacing between the substrate 26 and backer plate 32. The spacer 31 can be formed out of, for example, polydimethylsiloxane (PDMS). The PDMS may be cast on the rear surface of the substrate 26 through a mold produced using integrated circuit techniques to provide precisely controlled spacer thickness or may be spun-coated and selectively removed except at the edges of the substrate 26. Regardless of the particular manner in which the PDMS is incorporated into the multi-layered assembly 14, it is preferably configured to form a chamber defined by the PDMS at its outer perimeter and defining a space between the substrate 26 and backer plate 32.

The space between the substrate 26 and the backer plate 32 is filled with energy absorbing material 34 which can be a liquid media and, in some embodiments, a UV absorbing organic liquid. The energy absorbing material 34 has thermal expansion and/or UV absorption coefficients that are large enough to heat and/or squeeze the substrate 26 to an extent that facilitates, catalyzes, or initiates laser drilling of the substrate 26. The energy absorbing material 34 can have a thermal expansion coefficient of at least about $700 \times 10^{-6} K^{-1}$ and a UV absorption coefficient of at least about $1.46\ cm^{-1}$, preferably being within a range of between about $1.46\ cm^{-1}$ to $1.65\ cm^{-1}$. Suitable UV absorbing organic liquids for use as energy absorbing material 34 include, for example, acetone and fluorescence immersion oil, along with other suitable materials that may increase temperature when exposed to UV radiation to an extent that may correspondingly heat the substrate material, interfacing therewith, so as to melt the substrate material. Examples of other suitable energy absorbing materials 34 include, but are not limited to, pyrene, naphthalene, and toluene, and/or other materials.

Still referring to FIGS. 2 and 3, the particular amount of volume of energy absorbing material 34 is selected based on the intended configuration of multi-layered assembly 14, and laser drilling techniques that are implemented, and intended end-use configuration and characteristics of substrate 26 for its use in a patch clamping setup. In some embodiments, a relatively small amount of energy absorbing material 34 is used by sandwiching a thin layer of the energy absorbing material 34 between backer plate 32 and substrate 26, without incorporating spacers 31. In other embodiments, such as the one illustrated in FIG. 2, a relatively greater volume of energy absorbing material 34 is provided, with the particular volume being a function of the space between the backer plate 32 and substrate 26 as dictated by spacer 31.

Regardless of whether the energy absorbing material 34 is implemented as a thin layer that is tightly sandwiched between the substrate 26 and a backer plate 32 substantially adjacent and below the substrate 26, or implemented as a thicker layer that fills a larger space between the substrate 26 and backer plate 32 as dictated by spacer 31, the energy absorbing material 34 and substrate 26 are preferably in a face-to-face or an abutting relationship with respect to each other. In such configuration, the substrate 26 and energy absorbing material 34 define an interface 35 therebetween. Interface 35 allows the energy absorbing material 34 to transmit heat and/or pressure to the substrate 26 with relatively little energy loss in so doing.

Figure 4:
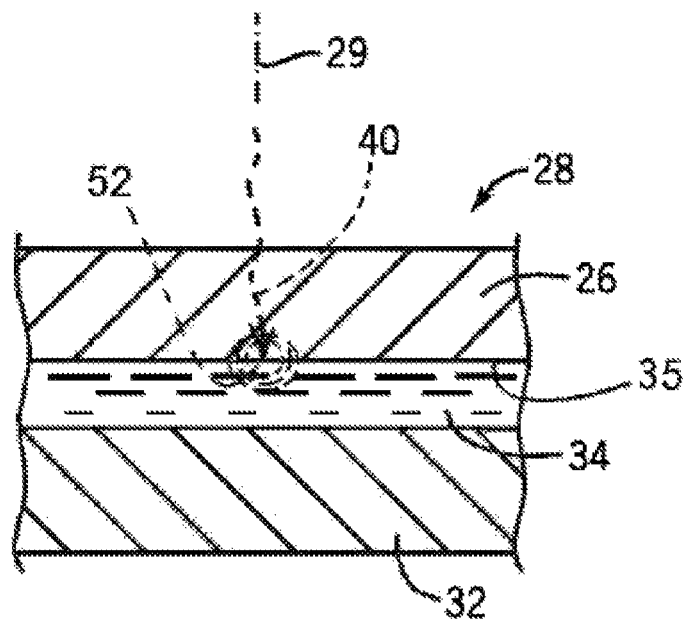
FIG. 4 is a figure similar to that of FIG. 3 showing an initial stage of laser micromachining in which a laser beam is focused toward an interface between the substrate and energy absorbing material.

Referring now to FIGS. 1 and 4, the laser 10 may be positioned above a first location 29 and pulsed by the controller 18 to produce a series of controlled light pulses 40 of laser beam 12 that is focused at the interface 35 or substantially adjacent or proximate thereto. The light pulses 40 are directed toward a front side 46, passing through an outer surface 47 thereof. Since substrate 26 is substantially transparent to UV light, the light pulses 40 pass through the entire thickness of the substrate 26, leaving the substrate 26 through an outer surface 49 of a back side 48 of the substrate 26. At this point, the substrate 26 is substantially unheated or otherwise affected by the light pulses 40, at least compared to the temperature increase, thermal expansion, and/or other responses of the energy absorbing material to the stimulus of the light pulses 40.

Still referring to FIGS. 1 and 4, the laser 10 indirectly heats the substrate 26 by primarily heating the energy absorbing material 34 which, in turn, secondarily heats the substrate 26 at its back side 48 or from below. In particular, the light pulses 40 that are focused at the interface 35, heat the energy absorbing material 34 and therefore also the outer surface 49 of the back side 48 of substrate 26 to establish rapid increases temperature and pressure at the interface 35. This correspondingly leads to rapid thermal expansion of the energy absorbing material 34 and/or exit side 48 of substrate 26 that can lead to an ablation of material from the exit side 48 or, in some embodiments, create a shock wave 52 at the interface 35. In any event, a one-step emission of the laser 10 may be used for wholly fabricating a crater 53 and/or pore 54 in the substrate 26, explained in greater detail elsewhere herein. The particular configuration and characteristics of the crater 53 and/or pore 54 are influenced by, amongst other things, the particular setup of the laser 10 and its output qualities, described in greater detail elsewhere herein, whereby the craters 53 and/or pores 54 are give desired sizes, shapes, and/or other characteristics by selecting a corresponding setup and output qualities of the laser 10.

Referring now to FIGS. 5-8, shows an embodiment of crater 53 that can be a disc-shaped depression extending into the back side 48 of the substrate. Crater 53 has a relatively flat bottom wall 102 that can have a circular perimeter shape and extend generally parallel to the outer surface 49 of back side 48. Seen best in the SEM (scanning electron microscope) image of FIG. 8, crater 53 of this embodiment includes a sidewall 105 that may taper slightly inwardly toward the bottom wall 102. An upper portion of sidewall 105, in its orientation of FIG. 8, transitions into the outer surface 49 of back side 58 by way of an arcuate surface that may have been at least partially smoothed during its formation. The smoothing is analogous to the smoothing achieved on an exponentially larger scale with open flame fire polishing, for example, while fire polishing a pipette or some other structure that is exponentially larger than the crater 53 and/or pore 54.

Intuitively, overall dimensions of the crater 53 are functions of dimensions and characteristics of the sidewall 105. Stated another way, crater 53 defines a crater depth which corresponds to a height dimension of the sidewall 105. A crater width or diameter is defined by a (greatest) distance measured between facing surfaces of the sidewall 105. As can be extrapolated from the size scale provided in FIG. 8, crater 53 may have a crater diameter of about 40 μm and a crater depth of about 10 μm.

In some embodiments, along at least part of the perimeter of crater 53, an undercut 110 extends radially into the sidewall 53, between the sidewall and the bottom wall 102. Such undercut 110 may define a groove as an interlocking structure into which portions of a cell can flow under certain conditions, allowing parts of the cell's membrane to engage against, for example, a projecting shoulder defined between the undercut 110 and sidewall 105.

Figure 7:
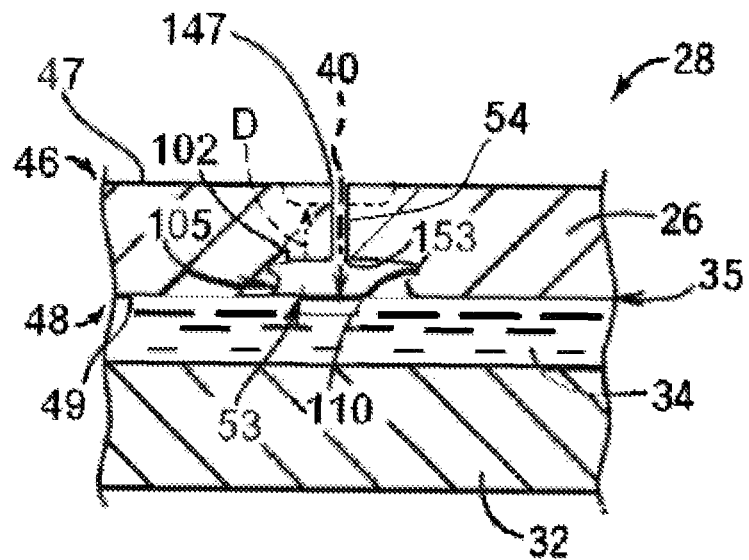
FIG. 7 is a figure similar to that of FIG. 5 showing the pore after completion of the drilling procedure.
Figure 8:
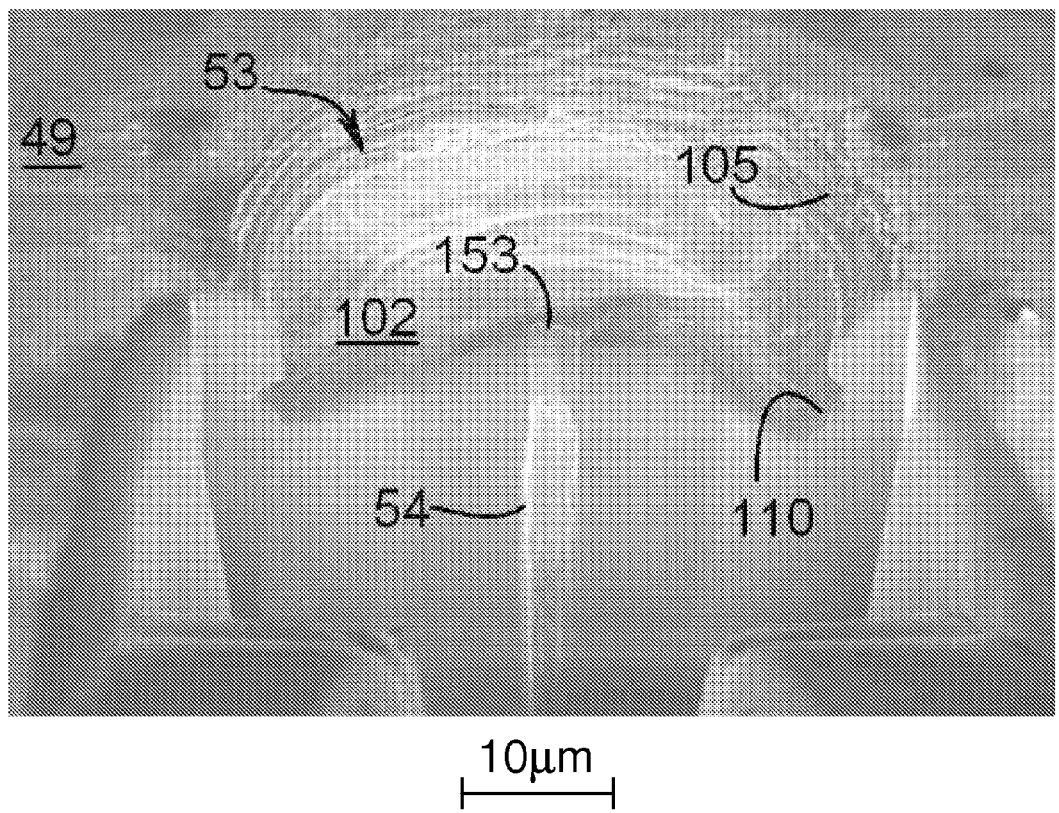
FIG. 8 is an enlarged scanning electron microscope image of a substrate after focused ion beam milling to show a cross-section of a first embodiment of a substrate that was laser micromachined according to methods of the invention.

Referring now to FIGS. 7 and 8, after completion of the laser micromachining of substrate 26, a smoothed annular edge or shoulder can define an opening between the crater 53 and a pore 54, such opening being labeled as a pore-crater opening 153. Like various portions of the crater 53, the pore-crater opening 153 can be fire polished and smoothed so as to eliminate substantially all surface irregularities. Seen best in FIG. 8, the pore-crater opening 153 maybe located in the middle of bottom wall 102 of the crater.

The pore 54 extends between the pore-crater opening 153 and a pore-surface opening 147 that opens into the pore 54 from the outer surface 47 of the front side 46 of substrate 26. Accordingly, in embodiments of substrate 26 that include a crater 53 formed thereinto, pore 54 extends between the crater 53 and the front side 46. In embodiments of substrate that do not include a crater 53, the pore 54 extends between the front and exit sides 46, 48, in other words, through the entire thickness dimension of the substrate 26. Regardless of the particular end-use configuration of substrate 26, pore 54 has a substantially constant diameter along at least a major portion of its length. Accordingly, the pore-surface and pore-crater openings 147, 153 may define opening diameters that are about the same size, for example with the larger of the two openings being no more than about 50% greater than the smaller of the two openings. As another example, the pore 54 can define minimum diameter and maximum diameter segments along its length, with the maximum diameter segment being no more than about 50% greater in magnitude than the smaller diameter segment.

Referring to FIGS. 4-8, a crater 53 and/or pore 54 may be formed into substrate 26 of the multi-layered stack 14 in the following way. The multi-layered stack 14 is assembled and the laser 10 is set up to based on intended characteristics of the crater 53 and/or 54, such as pore diameter and/or others. As discussed above, light pulses 40 are focused away from the front side 46 of the substrate 26 and toward its interface 35 with the energy absorbing material 34. Doing so causes a thermal expansion and also pressure increase of the affected material(s) within the multi-layered stack 14, which may be largely the energy absorbing material 34 at this early stage. Correspondingly, the interface 35 and the back side 48 of the substrate 26 may be secondarily affected by the changes occurring within the energy absorbing material 34. Such secondary affects may be an indirect heating characteristic of laser 10, by way of the substrates' 26 intimate interaction with the energy absorbing material 34.

For example, by focusing the light pulses proximate the interface 35, increasing temperature and pressure of the energy absorbing material 34 can be transmitted to the substrate 26, establishing a localized zone of increasing temperature and pressure of the back side 48 nearest the point of focus of the light pulses 40. This may cause temperature and pressure differentials between the front and exit sides 46, 48 of the substrate 26 but in any event will increase temperature and pressure at the back side 48. When such values increase enough, a crater 53 and/or pore 54 can be established by way of this a one-step micromachining procedure.

Figure 5:
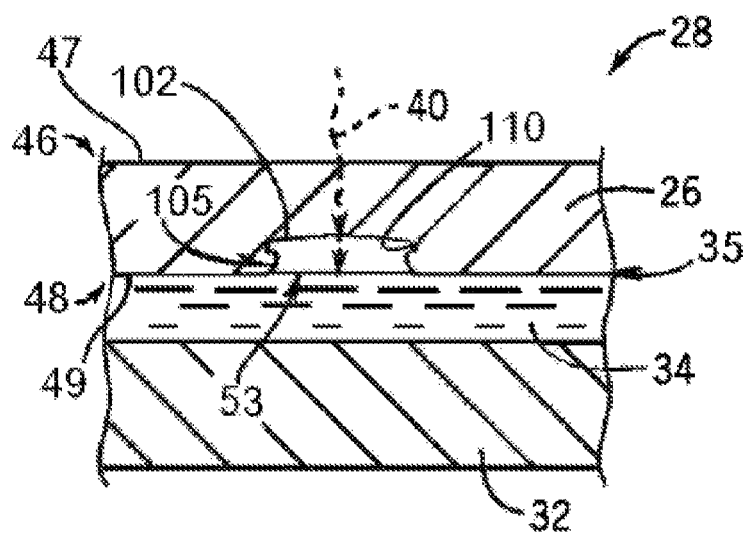
FIG. 5 is a figure similar to that of FIG. 3 showing transmission of energy through the substrate into the energy absorbing material after a crater has been formed in a back side of the substrate.
Figure 6:
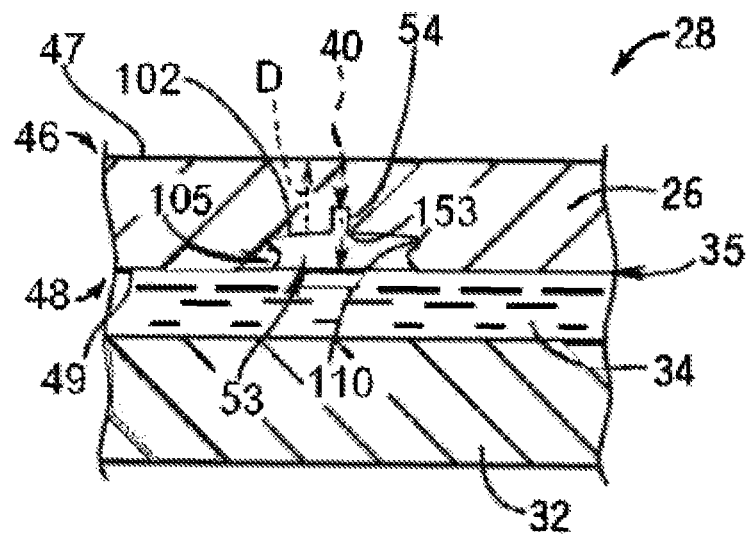
FIG. 6 is a figure similar to that of FIG. 5 showing an initiation of a pore drilling procedure.

Referring now to FIGS. 5-7, although the Applicant does not wish to be bound by a particular theory, it is contemplated that the formation of crater 53 may be an initiator of the drilling of pore 54. In such embodiments, once crater 53 is formed, the near molten material of bottom wall 102 is more receptive to accepting energy from or, in other words, is less transparent to the UV from laser 10 than material in a room temperature at-rest substrate 26. Accordingly, due to the preheating of bottom wall 102 during establishment of the crater 53, the light pulses 40 are able to further ablate material at their point of interaction with the preheated bottom wall 102, allowing the light pulses 40 to pierce therethrough and begin formation of the columnar pore 54.

Referring now to FIGS. 6 and 7, while the emission of light pulses 40 continues, so does the ablation or melting away of more material at the particular location which the light pulses 40 pass through the material of the substrate (FIG. 6). In this regard, the pore 54 may propagate upwardly toward the front side 46 of the substrate so as to define a drilling direction "D" that opposes the direction of the light pulses 40 passing through the substrate 26. In yet other embodiments, the pore 54 is not formed in the drilling direction "D" but instead, the drilling direction can extend in the same direction as the light pulses 40 passing through the substrate 26, whereby the pore 54 drilling may originate at the outer surface 47 of the front side 46. Although the terms "front" and "back" in describing various portions of the substrate 26 have been implemented in a convenient sense, it is fully contemplated that the by, for example, inverting the arrangement of the components of stack 14, or positioning the laser 10 on the opposing side of the stack 14, such terms might then assume generally opposite means. In other words, regardless of the particular orientation of the stack 14 and/or relative positions between the stack 14 and laser 10, in preferred embodiments, the drilling direction "D" extends from the interface 35 between the energy absorbing and substrate materials 34, 26, toward the side or outer surface of the substrate 26 that opposes the energy absorbing material. That is, the drilling direction "D" typically extends away from the location where the shock wave 52 occurred, whether such direction is the same as or opposite to the direction of laser 10 emission.

Regardless of how the pore 54 is created in a particular embodiment, the pore characteristics such as, for example, pore diameter, may be controlled or manipulated at least to some extent by adjusting the set up and controls of the laser 10. For some crater 53 and/or pore 54 formation procedures, the laser output power may be fixed at 5 W and a variable attenuator of the laser 10 can be set to allow about 70%, for example, 73% of total beam transmission, and operated for 2500 pulses at a 100 Hz repetition rate for the light pulses 40. Yet other set ups are contemplated, again, based on the intended characteristics of the crater 53 and/or pore 54 that are being formed.

For example, Table 1 below illustrates how pore diameter can be influenced by changing transmission rate or repetition rate of the emitted light pulses 40, from 50 Hz pulses to 100 Hz pulses during their emission from the laser 10. To establish such data of Table 1, laser energy was fixed at 50 mJ and six drilling schemes (Recipes) were tested to show various combinations of the two transmission rates, and the corresponding influence on pore diameter.

TABLE I

Drilling Recipes for Two Different Transmission Rates and Their Results

| Recipe | 50 Hz Pulses | 100 Hz Pulses | Pore Diameter (μm) at 83% Transmission Rate | Pore Diameter (μm) at 87% Transmission Rate |
|---|---|---|---|---|
| 1 | 3000 | 0 | 0.216[a] | 3.841 |
| 2 | 500 | 2000 | 0.621 | 4.168 |
| 3 | 1000 | 4000 | 0.342 | 4.455 |
| 4 | 1500 | 3000 | 0.395 | 4.511 |
| 5 | 2000 | 2500 | 1.594 | 5.270 |
| 6 | 2000 | 4000 | 3.210 | 5.421 |

[a]Note:
This approaches the laser wavelength limit of 193 nm.

Referring generally to FIGS. 8-11, the different configurations of these different embodiments show that, similar to the data in Table 1, influencing output characteristics of laser 10 may be used to form craters 53 and/or pores 54 that have different features, configurations, and/or other characteristics, as desired. Namely, using (relatively) higher transmission rates for laser 10, for example, transmission rates of greater than about 80%, produces craters 53 with flat bottom walls 102, like those seen in FIGS. 8-10. Using (relatively) lower transmission rates for laser 10, for example, transmission rates that are less than about 80%, produces craters 53 that have tapering sidewalls and substantially no discernable bottom wall, like that seen in FIG. 11.

Figure 9:
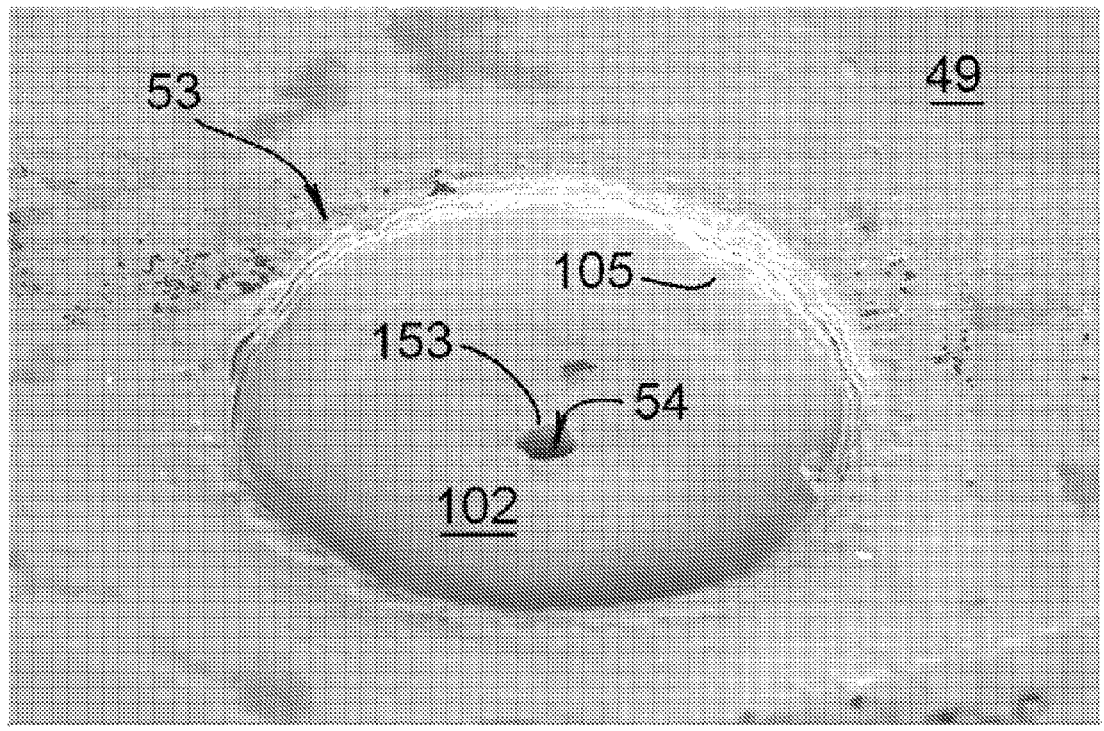
FIG. 9 is an enlarged scanning electron microscope image of a pictorial view of a variant of the substrate of FIG. 8.
Figure 10:
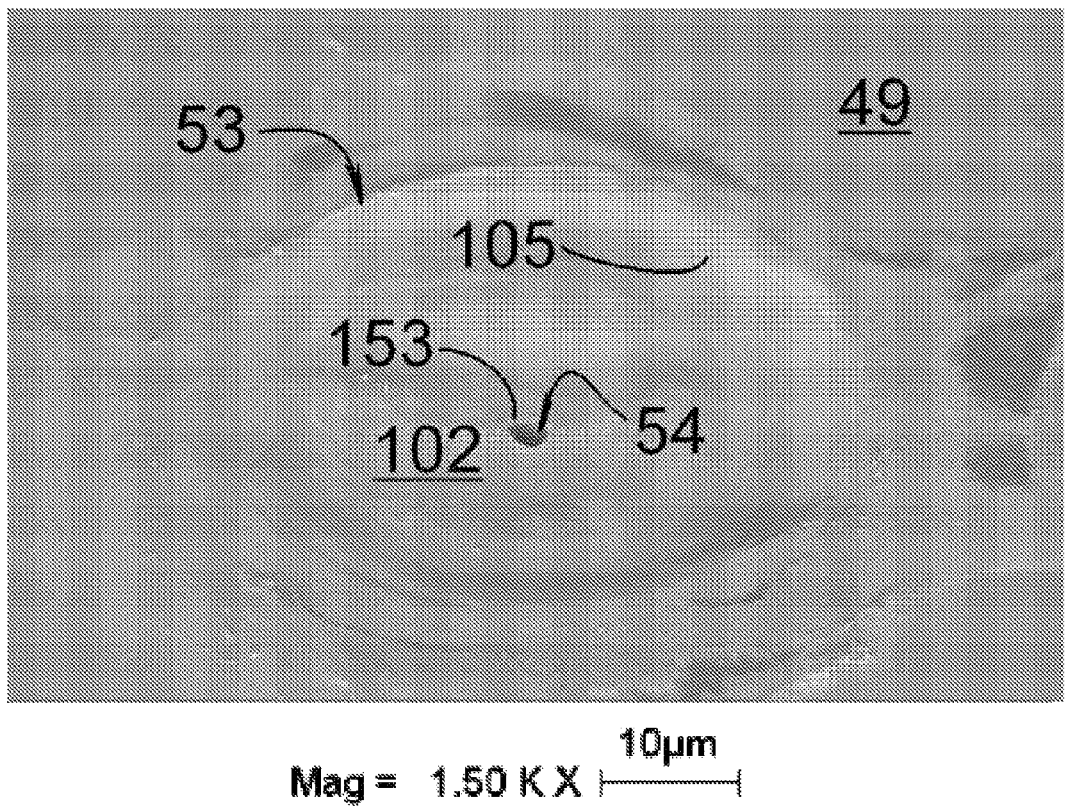
FIG. 10 is an enlarged scanning electron microscope image of a pictorial view of another variant of the substrate of FIG. 8.

Specifically regarding the embodiments of FIGS. 8-10, of the embodiments of craters 53 that have flat bottom walls 102 or semispherical configurations, crater depth and sidewall configuration can also be controlled by the transmission rate or power of laser 10. Of the three different embodiments shown in FIGS. 8-10, the embodiment of crater 53 of FIG. 10 has the most shallow crater depth and also has a semicircular or concave-up, arcuate transition between the bottom wall 102 and the sidewall 105. The crater 53 of FIG. 10 that was formed with a transmission rate of laser 10 of about 83%.

Again comparing the embodiments of FIGS. 8-10, the crater 53 of FIG. 9 has a deeper crater depth than that of FIG. 10 but is shallower than that of FIG. 8. The crater 53 of FIG. 9 has a similar semicircular or concave-up, configuration to that seen in FIG. 10, with a somewhat flatter bottom wall 102 when compared thereto. The crater 53 of FIG. 9 was formed with a transmission rate that is between 83% and 87% which was used in making craters 53 of FIGS. 10 and 8, respectively. The crater of FIG. 8 has been previously discussed and, when compared to the craters 53 of FIGS. 9 and 10, has the deepest crater depth and the flattest bottom wall 102, deviating the most from a semicircular cross-sectional configuration. As discussed elsewhere in greater detail, the crater 53 of FIG. 8 includes an undercut 110 that is defined between the bottom and sidewalls 102 and 105.

Figure 11:
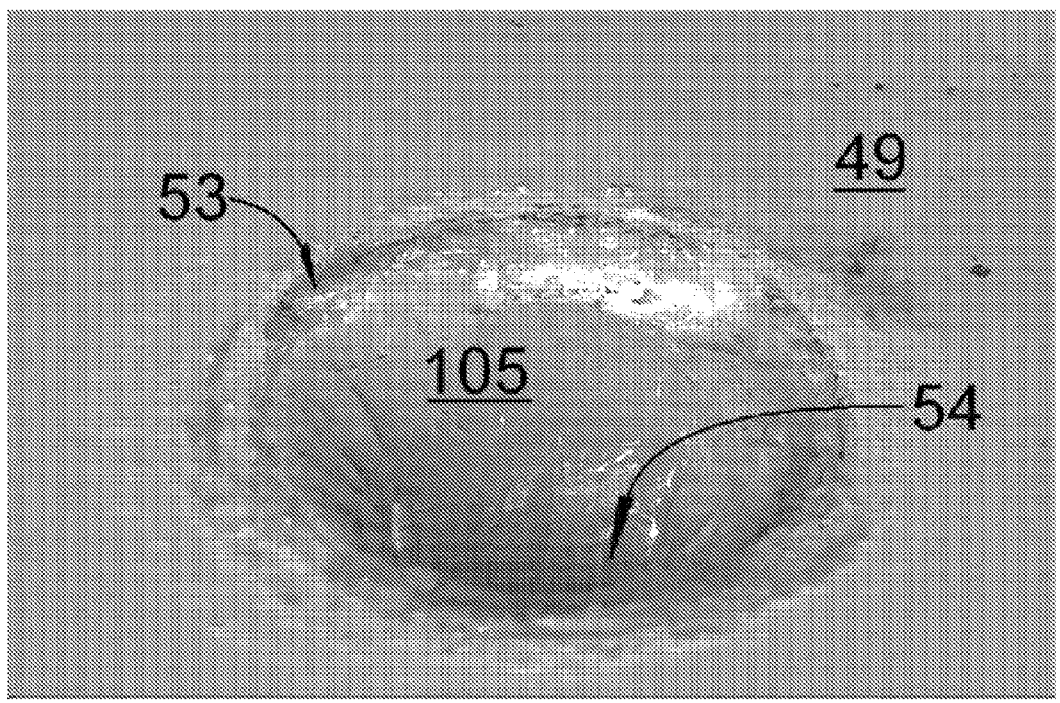
FIG. 11 is an enlarged scanning electron microscope image of a pictorial view of a second embodiment of a substrate that was laser micromachined according to methods of the invention.

Referring now to FIG. 11, this embodiment of crater 53 is made by setting the laser 10 to a relatively low transmission rate, for example, a rate of about 74%. This sub-80% transmission rate forms a crater 53 that appears trumpet-like or arcuately tapering in cross-section, such that the sidewall 105 tapers conically down to where it connects to the pore 54. The sidewall 105 can also, in some related embodiments, have scales or patterned discontinuities across surfaces thereof.

Figure 12:
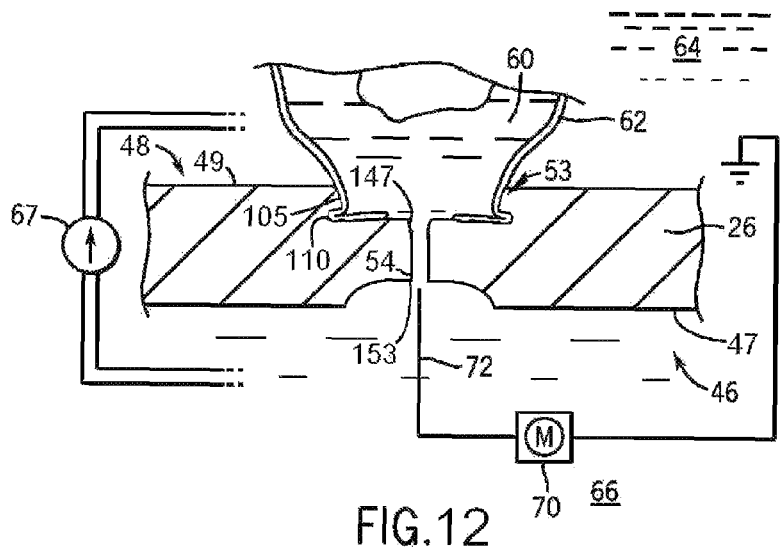
FIG. 12 is a simplified representation of the use of the substrate of FIG. 7 in a patch clamp application.
Figure 13:
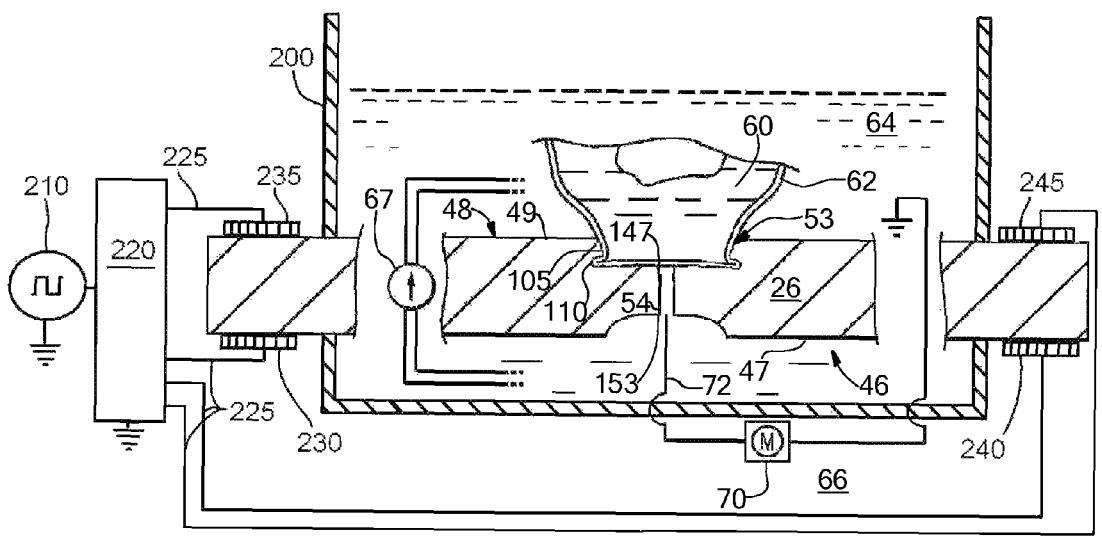
FIG. 13 is a simplified representation of another use of the substrate of FIG. 7 in a patch clamp application that incorporates piezoelectric actuation controls.

Referring now generally to FIGS. 12-13, regardless of the particular configuration of crater 53 and pore 54, after the substrate 26 has been laser micromachined into a usable wafer or chip having a crater 53 and/or pore 54, it can be implemented into a suitable investigative tool or instrument, depending on the particular intended end-use research or study that will be performed. It has already been shown that the craters 53 of the invention can provide gigaohm seals that are not only satisfactory in performance, but may be notably superior when compared to currently known techniques. For example, whereas known methods of glass chip production yield about 60% of produced units that can achieve 1.0-1.5 gigaohm seals, and a substantially lower percentage that can achieve about 5.0 gigaohm seals, preliminary mockup productions of glass chips using the inventive procedure(s) have already successfully produced a substantial percentage of produced units that have achieved 7.0 or greater gigaohm seals. In view of such promising preliminary results, it is fully contemplated and expected that the inventive methods disclosed herein are fully capable of producing chips that achieve or approach 15 gigaohm sealing capabilities.

Referring specifically now to FIG. 12, in some embodiments, the substrate 26 can be used in a planar patch clamp apparatus to investigate ion channel performance. As one example of such investigation, the substrate 26, shown having the same orientation as seen in FIG. 8 and therefore an inverted orientation with respect to that shown in FIG. 7, may receive a cell 60 within the crater 53 to expose a portion of the cell wall 62 to be accessible through the pore 54. A light suction applied by a pump 67 from the front side 46 may adhere the cell wall 62 to the surface of crater 53 with a 5 to 30 gigaohm resistance between a solution 64 on the side of the substrate 26 holding the cell 60 and a solution 66 on the side of the substrate 26 opposite solution 64. The application of suction may correspondingly also pull a portion of the cell wall 62 into the undercut 110 in a manner that enhances the seal of the cell 60 to the substrate 26 by way of the mechanical interlocking relationship therebetween. Although the cell 60 is shown in FIG. 12 as having its membrane or cell wall 62 ruptured over the pore 54, it is, of course, contemplated that the cell wall 62 remains intact for various other types of studies or investigations.

A sharp suction applied by a pump 67 at the outer surface 47 of the front side 46 or other means may be used to provide electrical connection to the interior of the cell 60 by a sensitive electrical detector 70 permitting measurement of electrical differences between the exterior and interior of the cell 60 through an electrode 72 communicating with the interior of the cell 60 referenced to solution 64 outside the cell 60.

Referring now to FIG. 13, since preferred embodiments of substrate 26 are made from a single crystal quartz material, such embodiments may be incorporated into an apparatus to investigate mechanosensitive ion channel performance and function. The apparatus of FIG. 13 is largely analogous to that of FIG. 12, only being configured to piezoelectrically actuate, stress, or otherwise stimulate the cell wall 62 so as to measure, by way of detector 70, gating responses of the particular ion channel that cooperates with the pore 54.

Still referring to FIG. 13, a bather 200 can be provided that acts as an enclosure, retaining the solution 64 therein. Ends of the substrate 26 extend through opposing sides of the barrier 200. A power source 210 provides electrical stimulus for stimulating the piezoelectric behaviors of the substrate. A controller 220 sends and controls an electrical signal to the substrate, through conductors 225 that lead to the substrate. The actual connection(s) of the conductors 225 to the substrate 26 can be accomplished with suitable terminals. For example, terminals 230 and 235 are attached to the opposing outer surfaces 46 and 47 at a first end of the substrate 26, appearing as a left end in FIG. 13, and connected to the controller 220 by a first pair of conductors 225. Terminals 240 and 245 are attached to the opposing outer surfaces 46 and 47 at a second end of the substrate 26, appearing as a right end in FIG. 13, and connected to the controller 220 by a second pair of conductors 225.

Referring yet further to FIG. 13, in such an embodiment, the controller 220 may place the cell wall 62 under compressive and/or tensile stresses along multiple axes of movement or actuation. Depending on the particular cut of the crystal, controller 220 may establish a voltage across the thickness of the substrate 26, specifically by establishing a voltage between the upper terminals 235, 245 and the lower terminals 230, 240. Depending on the polarity of the signal, doing so will cause the substrate 26 to compress or elongate with respect to its thickness dimension which correspondingly compresses or stretches the cell wall 62 in such direction. Here too, depending on the particular cut of the crystal, controller 220 may establish a voltage across the length of the substrate 26, specifically by establishing a voltage between the left end terminals 230, 235 and the right end terminals 240, 245. Again depending on the polarity of the signal, doing so will cause the substrate 26 to compress or elongate, only this time with respect to its length dimension, compressing or stretching the cell wall 62 in a corresponding manner. While doing so, the detector 70, senses notable gating and/or other responses of the particular ion channel or other portions of the cell 60, depending on the particular configuration of detector 70.

Referring yet further to FIG. 13, regardless of the particular configuration of the cell membrane investigating apparatus and its setup and controls, the substrate 26 according to the invention provides an "on-chip" piezoelectric system that may be used as a suitable alternative for imposing mechanical deformations to a membrane which to date has been primarily studied with pipettes and conventional patch clamping. Substrate 26 can be configured and implemented specifically for ones of, e.g., (i) lower frequency actuation of the ion channels, (ii) higher frequency mechanical probing, as well as (iii) static stress modulation of the membrane, as desired based on the particular investigation being performed.

It is specifically intended that the present invention not be limited to the embodiments and illustrations contained herein, but include modified forms of those embodiments including portions of the embodiments and combinations of elements of different embodiments as come within the scope of the following claims.

We claim:

1. A patch clamp chip for electrophysiology comprising:
a homogenous substrate selected from a group consisting of glass and quartz having a first outer surface and an opposing second outer surface;
a crater extending into one of the first and second outer surfaces and defining a crater diameter thereon; and
a pore extending between the crater and the other one of the first and second outer surfaces of the substrate, the pore defining a pore diameter that is smaller than the crater diameter and is generally constant along substantially the entire length of the pore, and wherein the length of the pore extends over a majority of a distance between the first outer surface and the opposing second outer surface of the substrate;
wherein at least one of the crater and the pore have a surface adapted to provide a gigaseal with respect to a cell membrane placed thereover.

2. The patch clamp chip of claim 1 wherein the single crystal quartz material has been pre-thinned by at least one of a laser etching and a wet etching procedure.

3. The patch clamp chip of claim 1, further comprising a shoulder defined between the pore and a generally flat bottom wall of the crater, wherein the shoulder comprises an angle of approximately 90 degrees, and wherein the shoulder defines a minimum diameter of the crater between respective diameters of the crater and pore.

4. The patch clamp chip of claim 3, the crater including (i) a crater depth being defined between a crater opening and the crater bottom wall, and (ii) a crater width being defined transversely across the crater bottom wall, and wherein crater width is at least two times greater than the crater depth in magnitude.

5. A patch clamp chip for electrophysiology comprising:
a substrate having a first outer surface and an opposing second outer surface;
a crater extending into one of the first and second outer surfaces and defining a crater diameter thereon; and a pore extending between the crater and the other one of the first and second outer surfaces of the substrate, the pore defining a pore diameter that is smaller than the crater diameter and is generally constant along a major portion of a length of the pore;

wherein the crater includes (i) a bottom wall, (ii) a sidewall extending outwardly away from the bottom wall, and (iii) an undercut that extends into the sidewall so as to define a sidewall shoulder between the undercut and the sidewall.

6. The patch clamp chip of claim 1 wherein the substrate is a piezoelectric material and the patch clamp chip further comprises electrical conductors that attach to the piezoelectric material at locations that are spaced from each other, the electrical conductors directing an electrical current therebetween that establishes a voltage across the piezoelectric material so as to piezoelectrically deform at least one of the first outer surface of the substrate, the second outer surface of the substrate, the crater, and the pore.

7. A patch clamp chip for electrophysiology comprising:
a homogenous substrate selected from a group consisting of glass and quartz having a first outer surface and an opposing second outer surface;
a crater defined by a sidewall having opposing facing surfaces and the sidewall defining a depth of the crater, the crater extending into one of the first and second outer surfaces and defining a crater diameter thereon defined by a greatest distance between the facing surfaces of the sidewall; and
a pore extending between the crater diameter and the other one of the first and second outer surfaces of the substrate, the pore defining a pore diameter that is smaller than the crater diameter and is generally constant along substantially the entire length of the pore;

wherein the pore further comprises (i) a pore-crater opening defining a pore-crater opening diameter defined at a location where the pore opens into the crater, and (ii) a pore-surface opening defining a pore-surface opening diameter defined at a location where the pore opens through an outer surface of the substrate material, and wherein the larger of the pore-crater and pore-surface opening diameters is no more than about 50% greater than the smaller of the pore-crater and pore-surface opening diameters;

wherein at least one of the crater and the pore are adapted to provide a gigaseal with respect to a cell membrane placed thereover.

\* \* \* \* \*